United States Patent
Hyde

(10) Patent No.: US 7,131,963 B1
(45) Date of Patent: Nov. 7, 2006

(54) CATHETERS AND METHODS OF USING CATHETERS

(75) Inventor: Gregory Matthew Hyde, Menlo Park, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 424 days.

(21) Appl. No.: 10/184,859

(22) Filed: Jun. 27, 2002

(51) Int. Cl.
*A61M 29/00* (2006.01)

(52) U.S. Cl. .............. 604/96.01; 604/101.01; 604/509

(58) Field of Classification Search ......... 604/96.01, 604/101.01, 101.03, 508, 509; 607/88, 120
See application file for complete search history.

(56) References Cited

U.S. PATENT DOCUMENTS

| | | | |
|---|---|---|---|
| 5,125,925 A | 6/1992 | Lundahl | |
| 5,196,005 A | 3/1993 | Doiron et al. | |
| 5,298,018 A | 3/1994 | Narciso, Jr. et al. | |
| 5,370,608 A * | 12/1994 | Sahota et al. | 604/20 |
| 5,397,307 A * | 3/1995 | Goodin | 604/103.07 |
| 5,454,794 A | 10/1995 | Narciso, Jr. et al. | |
| 5,456,661 A | 10/1995 | Narciso, Jr. | |
| 5,700,243 A | 12/1997 | Narciso, Jr. | |
| 5,709,653 A | 1/1998 | Leone | |
| 5,728,068 A | 3/1998 | Leone et al. | |
| 5,779,673 A * | 7/1998 | Roth et al. | 604/101.03 |
| 5,797,868 A | 8/1998 | Leone | |
| 5,976,175 A | 11/1999 | Hirano et al. | |
| 5,997,571 A | 12/1999 | Farr et al. | |
| 6,013,053 A | 1/2000 | Bower et al. | |
| 6,030,411 A | 2/2000 | Lawandy | |
| 6,054,449 A | 4/2000 | Robinson et al. | |
| 6,058,937 A | 5/2000 | Doiron et al. | |
| 6,086,558 A | 7/2000 | Bower et al. | |
| 6,096,030 A | 8/2000 | Ortiz | |
| 6,102,905 A | 8/2000 | Baxter et al. | |
| 6,113,588 A | 9/2000 | Duhaylongsod et al. | |
| 6,159,203 A | 12/2000 | Sinofsky | |
| 6,168,591 B1 | 1/2001 | Sinofsky | |
| 6,176,842 B1 | 1/2001 | Shunro et al. | |
| 6,270,492 B1 | 8/2001 | Sinofsky | |
| 6,682,499 B1 * | 1/2004 | Lenker | 604/4.01 |
| 6,905,476 B1 | 6/2005 | Ponzi | |

FOREIGN PATENT DOCUMENTS

| | | |
|---|---|---|
| WO | WO 98/51369 | 11/1998 |
| WO | WO 99/13943 | 3/1999 |

OTHER PUBLICATIONS

Adili, F. "Photodynamic Therapy With Local Photosensitizer Delviery Inhibits Experimental Intimal Hyperplasia," PubMed, Laser Sur. Med., 1998, vol. 28. No. 5, 1 page.

(Continued)

*Primary Examiner*—Kevin C. Sirmons
*Assistant Examiner*—Jaime Corrigan
(74) *Attorney, Agent, or Firm*—Blakely, Sokoloff, Taylor & Zafman LLP

(57) ABSTRACT

A catheter device and method, in which a first lumen coupled to a balloon, a second lumen coupled to the first lumen, the second lumen having a distal opening to dispense an oxygenated infusate, and a third lumen coupled to the second lumen and coupled to a second balloon. The second balloon restricts the flow of the oxygenated infusate, and the oxygenated infusate provides oxygen to tissue at a distal end of said catheter device.

14 Claims, 10 Drawing Sheets

OTHER PUBLICATIONS

Aveline, Béatrice M., "Environmental Effects On Cellular Photosensitization: Correlation of Phototoxicity Mechanism with Transparent Absorption Spectroscopy Measurement," Photochemistry and Photobiology, 1998, vol. 68, No. 1, pp. 51-61.

Global Lighting Technologies, Inc., "A New Way to Extract Light," Available: http://www.glthome.com/tech1.htm, 2 pages.

Gonschiro, P. "Selective Hematoporphyrin Derivative (HMD) Application In Arterial Vessels Using A Porous Balloon Catheter Results In Equivalent Levels As Compared To High-Dose Systemic Administration," PubMed, Kardiol, Dec. 1991, vol. 80. No. 12, 1 page.

Mandrusov, Membrane-Based Cell Affinity Chromatography to Retrieve Viable Cells, Biotechnol, Prob. 1995, 11, 208-213, Artificial Organs Research Laboratory, Department of Chemical Engineering, Material Science and Metallurgy, Columbia University, New York, New York 10027, and Lousville, Lousville, Kentucky 40292.

Assmus, Transplantation of Progenitor Cells and Regeneration Enhancement in Acute Myocardial Infarction (TOPCARE-AMI), Clinical Investigation and Reports, Oct. 8, 2002, pp. 3009-3017, Department of Molecular Cardiology and Department of Hematology H.M., D.H.) University of Frankfurt, Frankfurt, Germany, Circulation available at http://www.circulationha.org DOI: 10.1161/01.CIR.0000043246.74879CD.

* cited by examiner

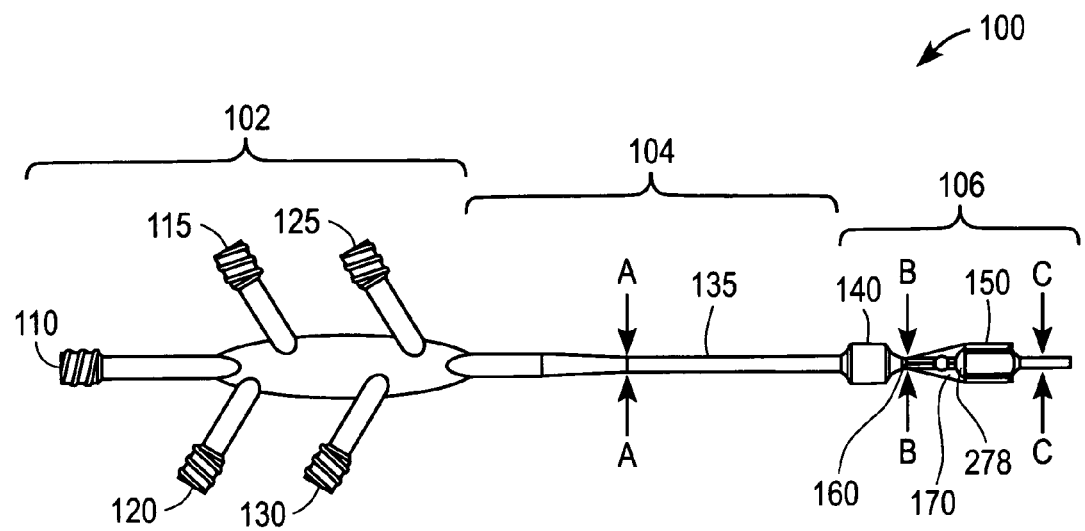
FIG. 1
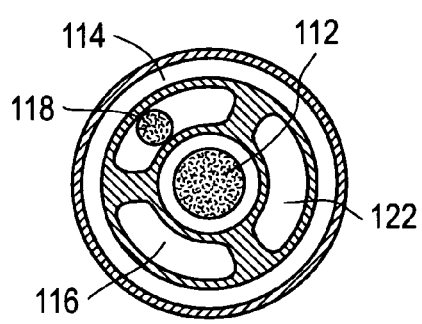
FIG. 1A-A
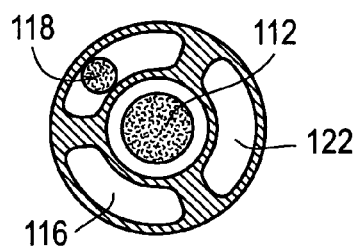
FIG. 1B-B
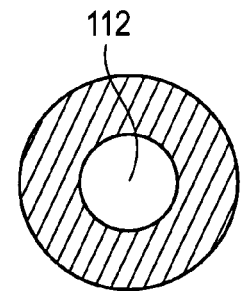
FIG. 1C-C

CATHETERS AND METHODS OF USING CATHETERS

FIELD OF THE INVENTION

The invention, in one embodiment, relates generally to the treatment of coronary disease, and more particularly, in one embodiment, to the delivery of a therapeutic light activated drug.

BACKGROUND OF THE INVENTION

Atherosclerosis, a process in which the walls of the arteries thicken due to the accumulation of plaque in the blood vessels, is the cause of most coronary artery disease that can result in heart attacks, strokes, or inadequate circulation to the extremities. Arterial occlusions caused by plaque accumulation may necessitate major invasive surgery, such as a coronary by-pass procedure. However, less invasive, percutaneous methods may be an alternative in treating atherosclerosis. For example, percutaneous transluminal coronary angioplasty (PTCA) involves advancing a balloon catheter through a body lumen to a target treatment site. In one example, a small incision is made near the femoral artery to insert the catheter, which is then advanced to a plaque area in the coronary artery. The catheter has a deflated balloon near a distal end, and the balloon is positioned across the plaque. Once in position, the balloon is inflated to crack or flatten the plaque, thereby restoring the normal patency of the blood vessel. The balloon is then deflated so that the catheter can be removed, allowing blood flow to resume through the dilated blood vessel.

Another percutaneous catheter treatment method involves drug delivery catheters, which may be used alone or in combination with angioplasty balloons. For example, balloons having micropores may be used to deliver a therapeutic bioactive agent to break-up plaque build-up. One disadvantage of drug delivery catheters that utilize balloons is that the drug, once released from the catheter, requires sufficient time to diffuse into the vessel wall of the treatment site. Otherwise, the drug would be washed downstream by the blood flow. In order to provide sufficient resonance time for diffusion of the drug into the vessel wall, temporary blockage of blood flow upstream from the treatment site may be required. As such, a balloon may be expanded upstream from the treatment site to block blood flow. However, if blood flow is obstructed too long, tissue and organs downstream of the inflated balloon may suffer ischemic damage from lack of oxygenated blood. Ischemia occurs when there is an imbalance between oxygen supply and demand, usually caused by clogged arteries, that leads to insufficient oxygen to tissues such as the heart or brain. The two most common types of ischemia are cardiac and cerebral. Cardiac ischemia includes a continuum of conditions, from silent ischemia to angina to acute myocardial infarction (AMI or "heart attack"). Cerebral ischemia includes transient ischemic attacks (TlAs) and stroke. Consequently, the desired dose to a treatment site may not be achieved in a single procedure because the efficiency of drug diffusion into the vessel wall is not optimized, requiring multiple catheter procedures to adequately treat the target site.

Studies have shown that light activated drugs may be used to treat atherosclerosis. However, ischemia risks may be present with the delivery of light activated drugs. The light activated drug is sensitive to light at a specific intensity or frequency, subsequently targeting cells that have absorbed the drug. However, once released into the blood stream near a target treatment area, the drug requires a certain amount of exposure time to the light for activation, as well as time for the drug to be absorbed into the vessel wall of the treatment site. In order to increase the resonance time to deliver effectively a light activated drug, blood flow needs to be obstructed upstream of the drug delivery area, but this creates the danger of causing ischemia to tissue downstream from the target treatment site.

SUMMARY OF THE INVENTION

A catheter device and method are described, in which, in one embodiment, a first lumen is coupled to a balloon, a second lumen is coupled to the first lumen, and the second lumen has a distal opening to dispense an oxygenated infusate. A third lumen is coupled to the second lumen and is coupled to a second balloon. The second balloon restricts the flow of the oxygenated infusate, and the oxygenated infusate provides oxygen to tissue at a distal end of said catheter device.

BRIEF DESCRIPTION OF THE DRAWINGS

The present invention is illustrated by way of example, and not limitation, in the figures of the accompanying drawings in which:

FIG. 1 illustrates one embodiment of a drug delivery catheter with cross-sectional views FIG. 1A-A, FIG. 1B-B, and FIG. 1C-C.

DETAILED DESCRIPTION

Figure 2:
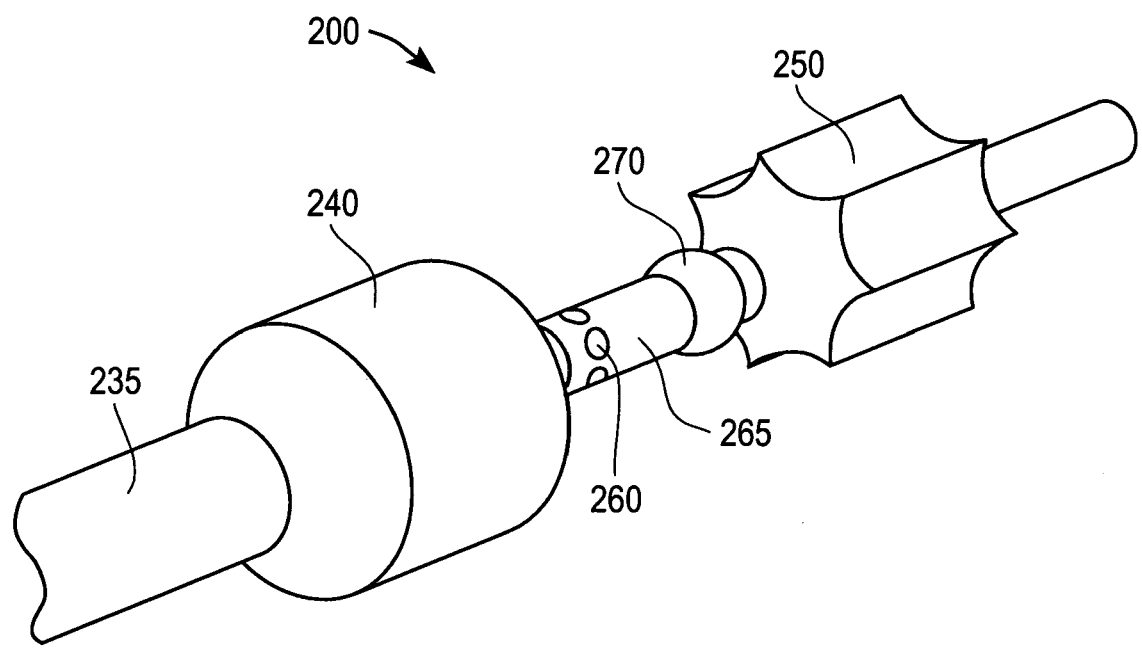
FIG. 2 illustrates one embodiment of a distal end of a drug delivery catheter.

In the following description, numerous specific details are set forth such as examples of specific, components, processes, etc. in order to provide a thorough understanding of various embodiment of the present invention. It will be apparent, however, to one skilled in the art that these specific details need not be employed to practice various embodiments of the present invention. In other instances, well known components or methods have not been described in detail in order to avoid unnecessarily obscuring various embodiments of the present invention.

Various embodiments of an apparatus and its method of use to deliver a bioactive infusate or drug within a body vessel are described. In one embodiment, an elongated intraluminal catheter with a drug delivery portion near a distal end is used to deliver an infusate within a body lumen. The drug delivery device has a first inflatable member to obstruct blood flow and a second inflatable member to impede, but not completely block, downstream flow of infusate. Infusion ports are disposed between the first and second inflatable members to release the infusate. Because the second inflatable member impedes downstream flow of infusate, the catheter provides an increased resonance time for the infusate to diffuse into a vessel wall. In one embodiment, the infusate may be an oxygenated cardioplegia solution. The oxygenated cardioplegia solution supplies oxygen to tissue downstream of the first and second inflatable members drug delivery device, thereby prolonging drug delivery time and preventing ischemic effects by the blockage of blood flow by the catheter.

In an alternative embodiment, the drug delivery portion of the catheter may also have a light diffuser capable of activating a light activated drug or bioactive agent released from the infusion ports. In one embodiment, the light diffuser is disposed between the infusion ports and the second inflatable member. As such, the light diffuser may effectively activate the light activated drug before diffusing into a vessel wall. A light activated bioactive agent may be released from the infusion ports and subsequently activated by the light source. The light activated bioactive agent may be mixed with an oxygenated infusate to prolong a treatment delivery time without risking ischemic damage. The drug delivery catheter may be utilized to deliver bioactive agents for the treatment of cardiovascular disease, such as atherosclerosis, or any number of diseases localized or treatable from a body lumen.

In one embodiment, the catheter has multiple lumens to utilize the various parts of the drug delivery portion. The catheter may be an over-the-wire type in which a guidewire lumen extends from the proximal end of the catheter to the distal end, and enables the catheter to advance over the guidewire to a location in the patient's body lumen. A first expandable or inflatable member lumen extends from the proximal end of the catheter to the first inflatable member, such as a balloon. A second inflatable member lumen extends from the proximal end of the catheter to the second expandable or inflatable member, such as a balloon. An infusion lumen extends from the proximal end of the catheter to the infusion ports to release perfusate and/or drug to a location between the two expandable members. A lumen extends from the proximal end of the catheter to the light diffuser containing a means to transfer light or energy from the proximal end of the catheter to the light diffuser. This may be accomplished by a fiber optic member that delivers light to the light diffuser. Alternatively, a light source may be disposed directly behind the light diffuser in which an electrical cable connected to a power source supplies electricity to the light source. Alternatively, the light diffuser may be coupled to a laser. It will be appreciated that the term "light" includes any electromagnetic radiation, whether visible or not.

In one embodiment of a method of using the drug delivery catheter, the catheter is advanced to a desired location in the patient's body lumen (i.e., target location) by first inserting a guidewire through the body lumen to the treatment site. The catheter may also contain its own guide wire component to provide the catheter with the ability to steer its way to the target location. As an alternative to an over-the-wire catheter, a rapid exchange catheter delivery system may be utilized. As such, the catheter may be any of the catheter types used in the art, including but not limited to "rapid exchange" (RX) catheters, "over-the-wire" (OTW) catheters, or a "tip RX" catheters. The catheter is positioned so that the target site (e.g., the site where an infusate is to be eluted from the catheter) is between the first and second inflatable members. Once the catheter is advanced to the target treatment site, the first inflatable member is expanded to obstruct blood flow proximal to the treatment site. Next, an infusate is released from the infusion ports. In one embodiment, the infusate may be a bioactive agent. Alternatively, the infusate may be a light activated bioactive agent. The bioactive agent may also be mixed with a solution of oxygenated cardioplegia fluid.

The second inflatable member, disposed downstream from the infusion ports, is expanded to impede the distal run off of the bioactive agent, thereby providing greater resonance time for diffusion into the vessel wall of the treatment site. Because the second inflatable member allows for some downstream run-off of the bioactive agent, the oxygenated cardioplegia supplies oxygen to downstream tissue that was initially denied by the expansion of the first inflatable member. Alternatively, a perfusion lumen having an opening downstream from the second inflatable member may provide oxygenated blood (from an opening upstream from the first inflatable member) to tissue which is downstream from the first inflatable member (and preferably downstream from the second inflatable member). As such, the catheter may be placed in the body vessel near the treatment area for greater time periods compared to a drug delivery catheter without oxygenated cardioplegia. Alternatively, if a light activated bioactive agent is released, a light source may be activated to diffuse a light from a light diffuser, also disposed between the first and second inflatable members, and projected toward the vessel wall to activate the drug. In an alternative embodiment, a light source may be incorporated into the distal shaft where it may directly deliver light to the light diffuser.

Turning now to FIG. 1, a perspective view of one embodiment of a drug delivery catheter 100 is illustrated. Proximal region 102 of drug delivery catheter 100 has guidewire port 110, first inflatable member port 115, proximal infusion port 120, second inflatable member port 125 and light diffuser port 130. The ports are coupled to a body that is in fluid communication with an elongated middle portion 104, which in turn is in fluid communication with drug delivery portion 106. Middle portion 104 has an elongated section appropriately sized to cover the distance required for drug delivery portion 106 to reach a treatment site. For the purpose of illustrating catheter 100 in its entirety, middle portion 104 is shown proportionately shorter than it would be relative to the ports and drug delivery portion. A working model of catheter 100 may have middle portion 104 long enough to cover distances analogous to catheters used for PCTA procedures. Drug delivery portion 106 is disposed near a distal end of drug delivery catheter 100, and includes first inflatable member 140, infusion ports 160, and second inflatable member 150. Optionally, drug delivery portion 106 may also have light diffuser 170 to be directed at infusate released from infusion ports 160.

The embodiment illustrated in FIG. 1 has, near a proximal portion, 5 lumens (shown along cross section in FIG. 1A-A) corresponding to ports 110, 115, 120, 125 and 130. Cross-sectional views FIG. 1A-A, FIG. 1B-B, and FIG. 1C-C illustrate the relationship, in one embodiment, of each port of catheter 100 with its respective lumen from middle portion 104 towards drug delivery portion 106 of catheter 100. FIG. 1A-A, taken near elongated middle portion 104, illustrates fourth lumen 112, first lumen 114, third lumen 116, fifth lumen 118, and second lumen 122. Guidewire port 110 is in fluid communication with a guidewire lumen 112 that extends along the entire length of drug delivery catheter 100 from a proximal end to a distal end. Guidewire lumen 112 enables drug delivery catheter 100 to be advanced over a guidewire (not shown) to a treatment site in a body vessel. First inflatable member port 115 is in fluid communication with first inflatable member 140 via lumen 114 to provide a conduit to pass an inflation medium (e.g., fluid) to expand first inflatable member 140. Second inflatable member port 125 is in fluid communication with second inflatable member 150 via lumen 116 to provide a conduit to pass an inflation medium to expand second inflatable member 150. Proximal infusion port 120 is in fluid communication with distal infusion ports 160 via lumen 122 to provide a conduit to pass a bioactive agent through catheter 100 to a target region in a body vessel. A variety of bioactive fluids may be passed through catheter 100, including but not limited to drugs to treat atherosclerosis and oxygenated cardioplegia solutions. In one embodiment, light diffuser port 130 is in fluid communication with light diffuser 170 (e.g., through lumen 118), which is capable of directing light from drug delivery portion 106 after a light activated drug or bioactive agent has been released from distal infusion ports 160. Light from diffuser 170 activates the drug to provide therapeutic effects to a target treatment area.

The cross-sectional view FIG. 1B-B, taken along a region between first inflatable member 140 and second inflatable member 150, has one less lumen compared to FIG. 1A-A. At this cross-sectional point, lumen 114 is not present because first inflatable member 140 is proximal to distal infusion ports 160. As such, lumen 112 corresponding to guidewire port 110, lumen 116 corresponding to second inflatable member 150, lumen 122 corresponding to distal infusion port 160, and lumen 118 corresponding to light diffuser 170 are present. The cross-sectional in FIG. 1C-C, taken along a region distal to second inflatable member 150 illustrates a single lumen 112 corresponding to guidewire port 110. Near the very distal end of catheter 100, the only lumen present is guidewire lumen 112. The five lumens that are disposed near the proximal end of catheter 100 terminate along various points of catheter 100 in the direction of the distal end. As such, in an over-the-wire type of drug delivery catheter, only guidewire lumen 112 extends continuously from a proximal end to a distal end of catheter 100.

FIG. 2 illustrates a perspective view of one embodiment of distal end 200 of catheter 100 (of FIG. 1). Elongated catheter portion 235 is coupled to first inflatable member 240. A second elongated portion 265 couples first inflatable member 240 to second inflatable member 250. A number of infusion ports 260 are disposed around second elongated portion 265. In one embodiment, first inflatable member 240 and second inflatable member 250 may be inflatable balloons. They may be made of a number of expandable materials, including polymers known and practiced in the art of catheter balloons. First inflatable member 240 and second inflatable member 250 are shown having different shapes. First inflatable member 240 is shown in an expanded state, evenly expanded around its outer surface. In contrast, second inflatable member 250 has a variable diameter that forms perfusion paths along its outer surface. Infusion ports 260 are disposed between first inflatable member 240 and second inflatable member 250. A variety of bioactive agents may be released from infusion ports 260 including, but not limited to drugs to treat atherosclerosis, anti-inflammatory agents, or similar bioactive agents to treat vessel occlusions. Additionally, a mixture of bioactive agents in a cardioplegia solution may be released from infusion ports 260.

Discussed in greater detail below with respect to the method of using drug delivery catheter 100, first inflatable member 240 and second inflatable member 250 are shaped differently to control the flow of blood or perfusate around the distal end of catheter 100. For example, first inflatable member 240 is shaped, when fully expanded, such that it makes continuous contact with the vessel wall near a target area to block blood flow upstream from infusion ports 260. Second inflatable member 250 is shaped, when fully expanded, such that it restricts downstream flow of fluid. Unlike first inflatable member 250, second inflatable member 260 does not completely block fluid flow.

Figure 6:
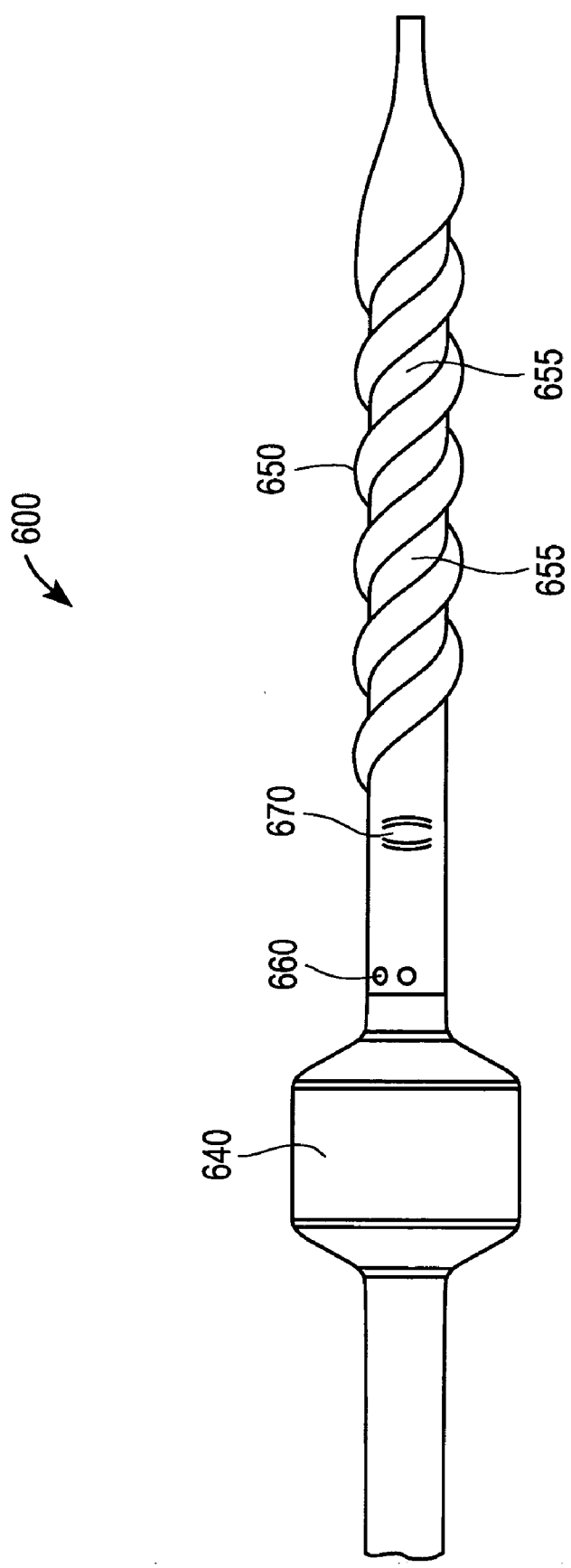
FIG. 6 illustrates one embodiment of a drug delivery catheter in which the second inflatable member is a helical balloon.

FIG. 6 illustrates a perspective view of an alternative embodiment of a drug delivery catheter 600 in which second inflatable member 650 is a helical balloon. Catheter 600 also has first inflatable member 640, infusion ports 660 and light diffuser 670. The spiral shape of the second inflatable member 650 forms a perfusion path 655 to allow downstream flow of the drug solution released from infusion ports 660. This embodiment is just another example of a balloon structure to reduce, but not completely block, the flow of a drug solution released from infusion ports 660. As such, the drug may be part of an oxygenated cardioplegia solution that provides oxygen to tissue downstream from drug delivery catheter 600. This enables catheter 600 to be placed in a body lumen for extended treatment periods without increasing the risk ischemia.

Returning now FIG. 2 bioactive agents are released downstream towards second inflatable member 250, the perfusion channels on second inflatable member 250 allow for restricted flow of bioactive agents past second inflatable member 250. The utilization of different obstruction member configurations may be especially useful in the delivery of oxygenated cardioplegia fluid. Blood flow blocked by first inflatable member 240 may be prolonged because tissue located downstream from the catheter 100 may still receive oxygen from the cardioplegia solution. The ability to provide longer drug delivery periods may avoid the need for multiple catheter treatment procedures. Moreover, the efficiency of a drug released from catheter 100 may be increased because the resonance time for the drug to be absorbed by the vessel wall around the target area is increased.

Distal portion 200 of the drug delivery catheter also has light diffuser 270 to disperse light between first inflatable member 240 and second inflatable member 250. In one embodiment, light diffuser 270 may be a lens or comparable light transparent material. In use, light is released from light diffuser 270 at a particular frequency/wavelength and intensity to activate light activated bioactive agent released from infusion ports 260. In one embodiment, light diffuser 270 is disposed distal to infusion ports 260 because the released light activated bioactive agent travels downstream toward second inflatable member 250. Light diffuser may be configured such that the activating light is focused in the direction of second inflatable member 250.

In an alternative embodiment, light diffuser 270 may be coupled to a light source disposed near a proximal end of drug delivery catheter. Light travels through a lumen (e.g., lumen 118 illustrated in FIG. 1) from a proximal end to light diffuser 270. In an alternative embodiment, the light source may be a fiber optic assembly built into the drug delivery catheter. A fiber optic light assembly allows light to travel through tortuous pathways of a body lumen without losing light intensity over long distances. Alternatively, a light source (e.g., a light emitting diode "LED") may be disposed adjacent to light diffuser 270. With the light source close to light diffuser 270, there may be minimal loss of light intensity over the elongated catheter. The light source may be electrically coupled to a power source near the proximal end of the drug delivery catheter.

Figure 2A:
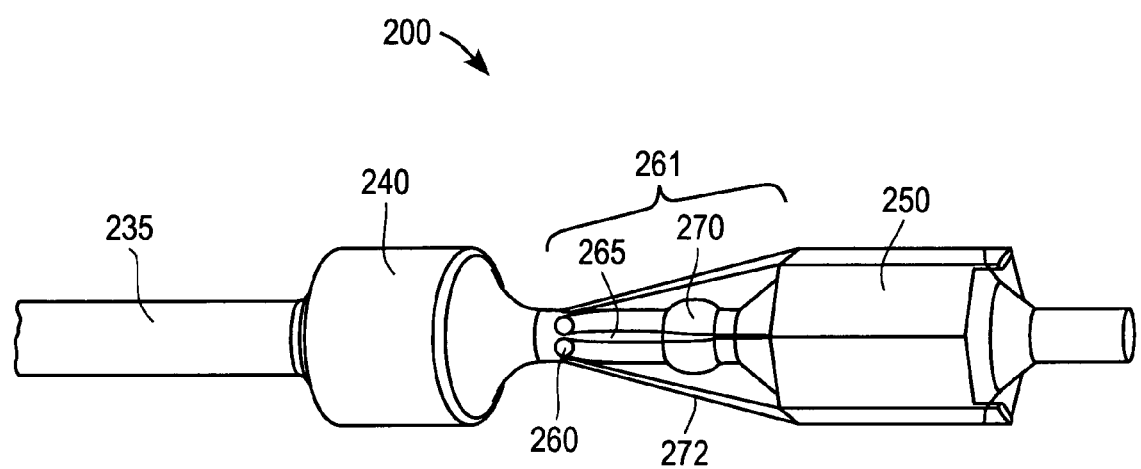
FIG. 2A illustrates another embodiment of a distal end of a drug delivery catheter.

FIG. 2A illustrates a perspective view of one embodiment of the distal end of a drug delivery catheter 200 after a light activated drug has been released and the light diffuser activated. First inflatable member 240 and second inflatable member 250 have been expanded to block blood flow and regulate the downstream flow of the light activated drug released from infusion ports 260. Shaded region 261 shows that the light activated drug has been released from infusion ports 260 and is traveling downstream towards second inflatable member 250. There will typically be some downstream flow as the drug is eluted from the ports 260 (under pressure from a drug delivery device (e.g., a syringe) at the proximal end which is coupled to the port 120). Highlighted region 272 within shaded region 261 shows light diffuser 270 has been activated within the light activated drug to activate it.

The phenomenon of photosensitization is typically dependent on frequency/wavelength and the intensity of the light. There are ranges for both frequency/wavelength and the intensity of the light, which span from no light activation of a drug to over-activation of a drug. Examples of light activated drugs include, but not limited to: Motexatin Lutetium produced by Pharmacyclics, which is activated by light at a frequency of 730 nanometers and an intensity of 180 Joules/cm$^2$; Tin Ethyl Etiopurpurin produced by Miravent, which is activated by light at a frequency of 662 nanometers and an intensity of 90 Joules/cm$^2$; 5-Amino-Levulinic Acid, which is activated by light at a frequency of 630 nanometers and an intensity of 50 Joules/cm$^2$; and Protoporphyrin IX, which is activated by light at a frequency of 630 nanometers and an intensity of 50 Joules/cm$^2$. The values stated for frequency and intensity are examples for the peak activation of each drug within a given range.

Figure 7A:
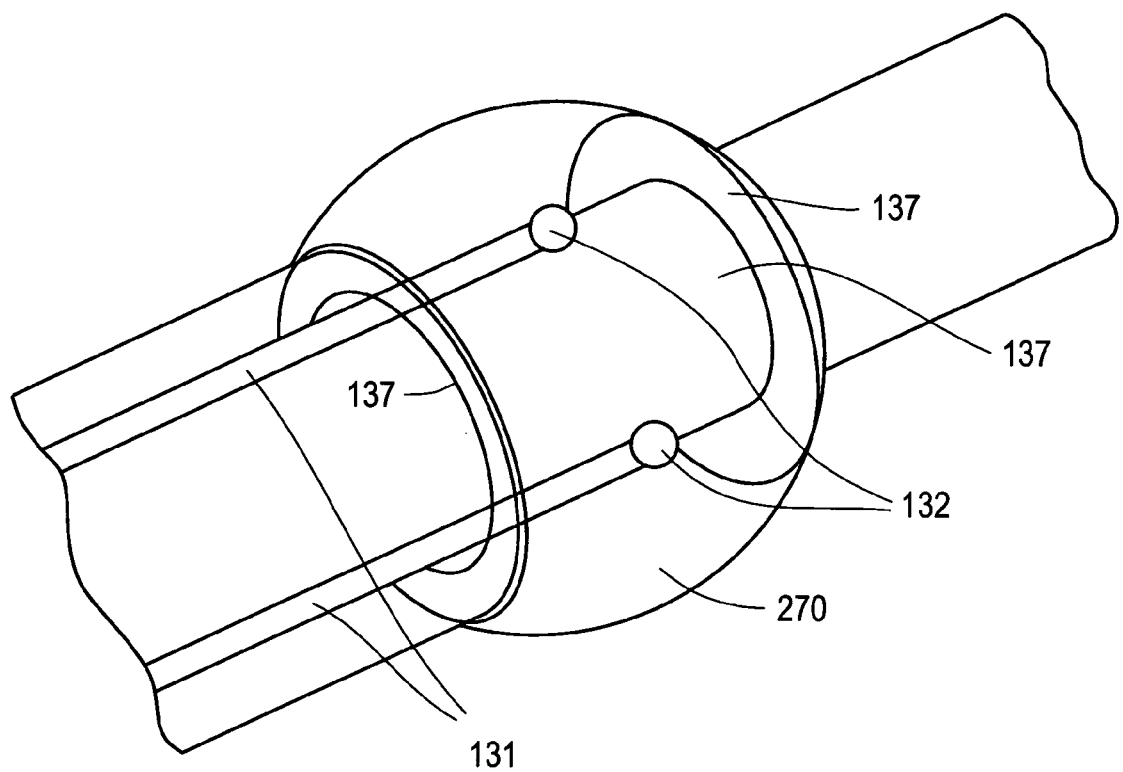
FIGS. 7A–7B illustrate perspective and cross-sectional views of one embodiment of a light diffuser.

FIG. 7A illustrates a perspective view of one embodiment of a light diffuser 270. A fiber optic member 131 is disposed in a lumen and allows light to travel through a lumen (e.g., lumen 118 of FIG. 1) proximal to the light diffuser 270. Disposed near distal end of fiber optic member 131, spherical end 132 directs light exiting the tip of the fiber optic member 131 away from drug delivery catheter shaft 265. The distal end of the fiber optic member 132 is embedded in glass light diffuser 270. End reflectors 137 prevent loss of light out of the proximal end, the distal end, and the inner surface of the light diffuser 270.

Figure 7B:
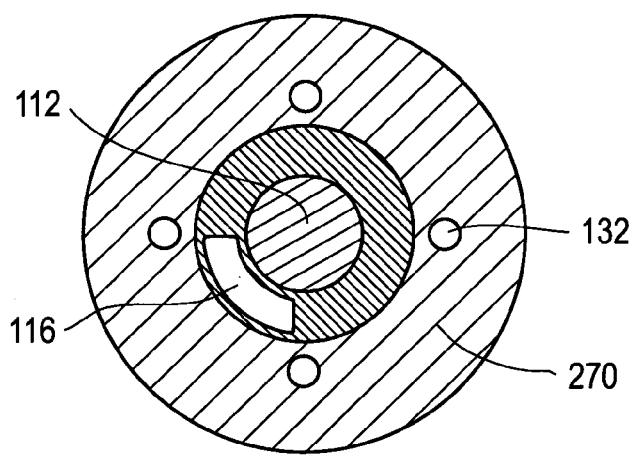

FIG. 7B illustrates a cross-sectional view of light diffuser 270 of FIG. 7A. The cross section view of FIG. 7B, taken through the center of the light diffuser 270, has guide wire lumen 112 that enables drug delivery catheter 100 to be advanced over a guide wire to a treatment site in a body vessel. Lumen 116 provides a conduit to pass an inflation medium to expand second inflatable member 150 and four spherical fiber optic tips 132. In this embodiment, four fiber optic members 132 are shown; alternatively, an array of one to multiple fiber optic members may be used.

Figure 8A:
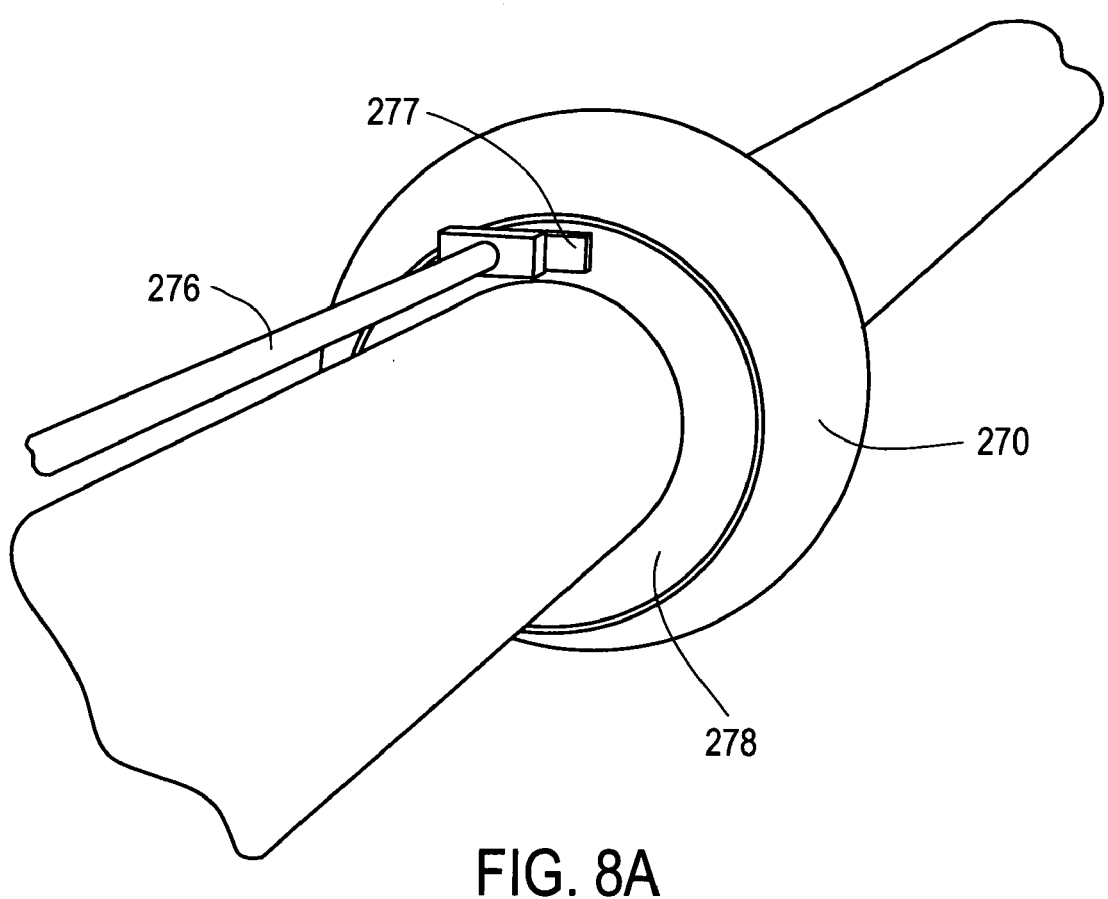
FIGS. 8A–8B illustrate perspective and cross-sectional views of another embodiment of a light diffuser.

FIG. 8A illustrates a perspective view of an alternative embodiment of the light diffuser 270. Electrical connection 276 travels through a lumen proximal to light diffuser 270. A LED light source 277 is embedded in glass light diffuser 270. End reflector 278 prevents loss of light out the proximal end, distal end, and inner surface of the light diffuser. In this embodiment one LED is shown; alternatively, an array of multiple LEDs could be used.

Figure 8B:
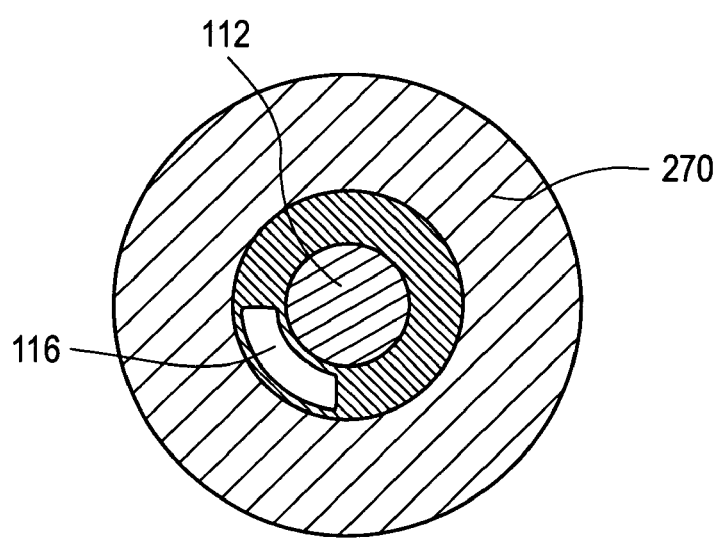

FIG. 8B illustrates a cross-sectional view of light diffuser 270 of FIG. 8A. Light diffuser 270 has guide wire lumen 112, which enables drug delivery catheter 100 to be advanced over a guide wire to a treatment site in a body vessel. Light diffuser 270 also has lumen 116, which provides a conduit to pass an inflation medium to expand second inflatable member 150.

Figure 9A:
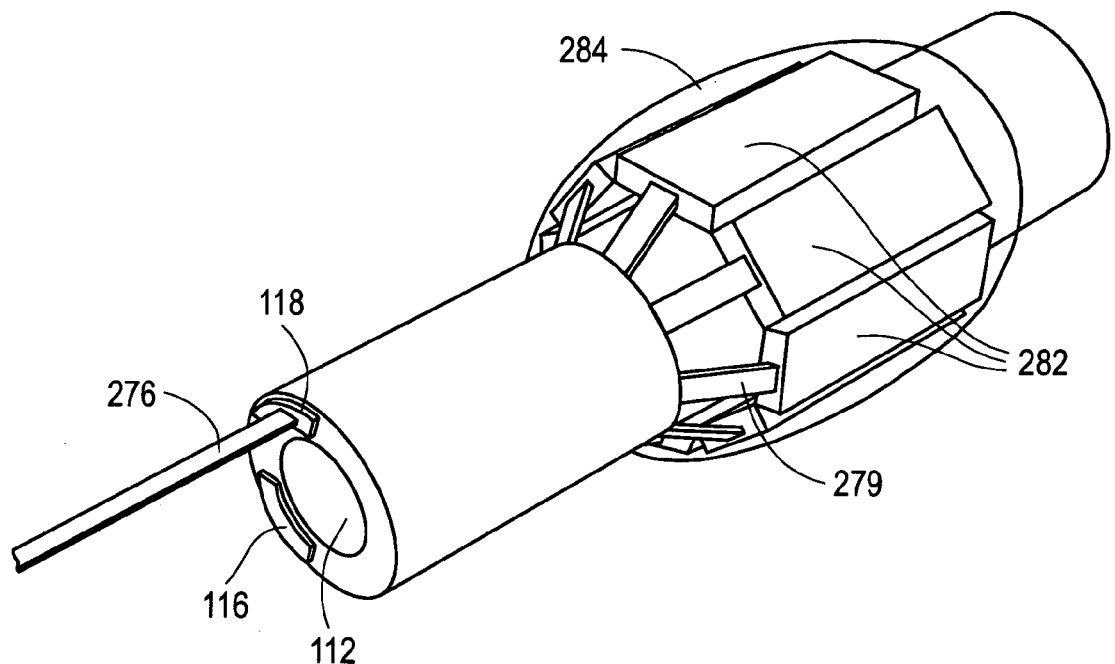
FIGS. 9A–9B illustrate perspective and cross-sectional views of another embodiment of a light diffuser.

The perspective view of FIG. 9A illustrates yet another alternative embodiment of light diffuser 270. Electrical connection 276 travels through a lumen proximal to the light diffuser 270. Electrical connection 276 may be connected to individual electrical connections 279 for each LED light source 282. Multiple LED light sources 282 may be embedded in a light transmitting material, polymer or adhesive 284.

Figure 9B:
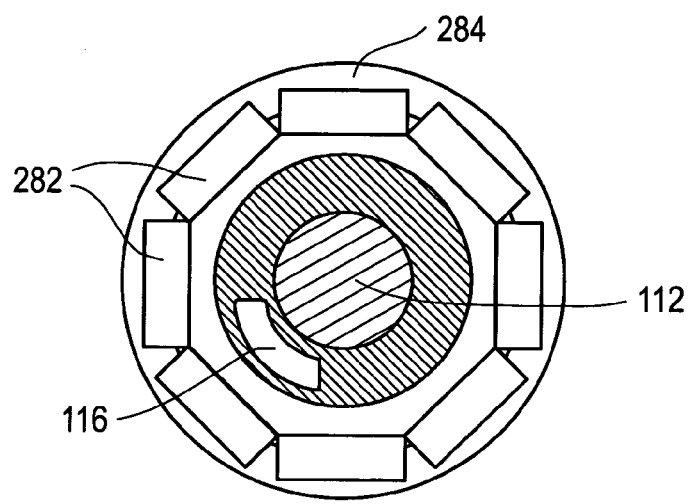

FIG. 9B illustrates a cross-sectional view of light diffuser 270 of FIG. 9A. Light diffuser 270 has guide wire lumen 112 that enables drug delivery catheter 100 to be advanced over a guide wire to a treatment site in a body vessel. Lumen 116 provides a conduit to pass an inflation medium to expand second inflatable member 150. In one embodiment, light transmitting material, polymer or adhesive 284 encapsulate light producing LED 282.

FIGS. 3A–3E illustrate, in one embodiment, a method of using a light activated, drug delivery catheter. Placement of catheter 300 is analogous to the insertion of catheters in PCTA procedures and is well known in the art. For example, an over-the-wire or rapid exchange may be utilized. In the method illustrated in FIGS. 3A–3E, guidewire 330 is inserted into arterial lumen 305. Drug delivery catheter 300 is advanced over guidewire 330 to a target location within arterial lumen 305. In this example, the target location may be a plaque region 310 that has formed to thicken arterial wall 320 within arterial lumen 305, resulting in occlusion of blood flow. Arrows 315 indicate the direction of blood flow through arterial lumen 305. Although this example illustrates treatment in an arterial lumen, use of catheter 300 in other body lumens other than arteries may be envisioned. For example, drug delivery catheter 300 may be appropriately sized for pulmonic placement or for placement in the urinary tract to treat occlusions or other body parts.

Figure 3A:
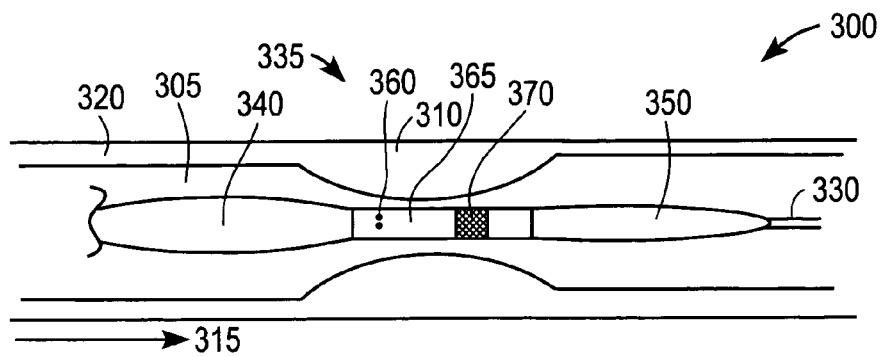
FIGS. 3A–3E illustrate a method of using a light activated, drug delivery catheter.

Distal portion 335 of catheter 300 has first inflatable member 340 and second inflatable member 350 coupled together by segment 365. Segment 365 has infusion ports 360 and light diffuser 370. As illustrated in FIG. 3A, catheter 300 is disposed within arterial lumen 305 such that plaque 310 is between first inflatable member 340 and second inflatable member 350, with infusion ports upstream from target site (e.g., plaque 310).

Figure 3B:
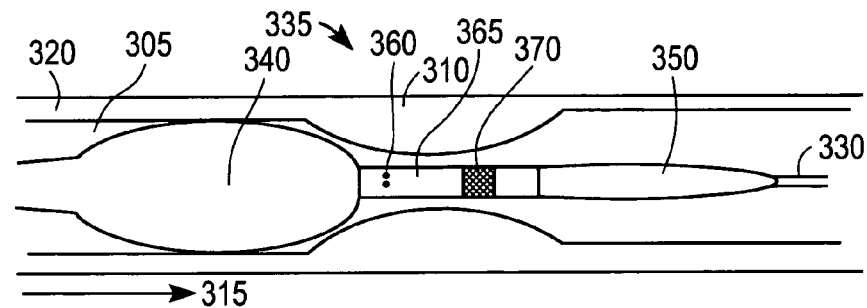
Figure 3C:
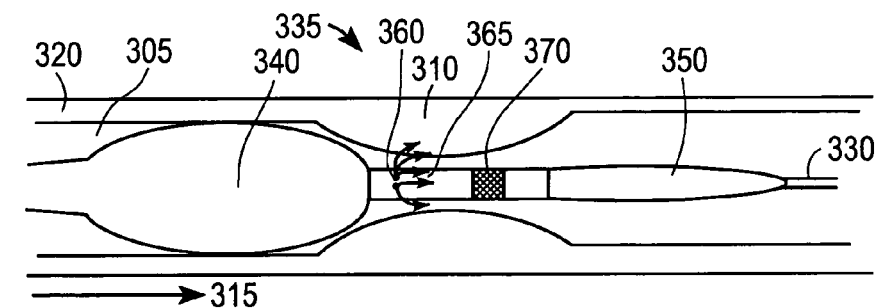
Figure 3D:
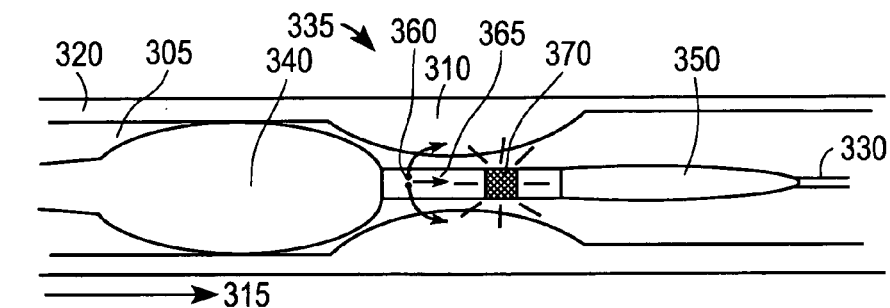
Figure 3E:
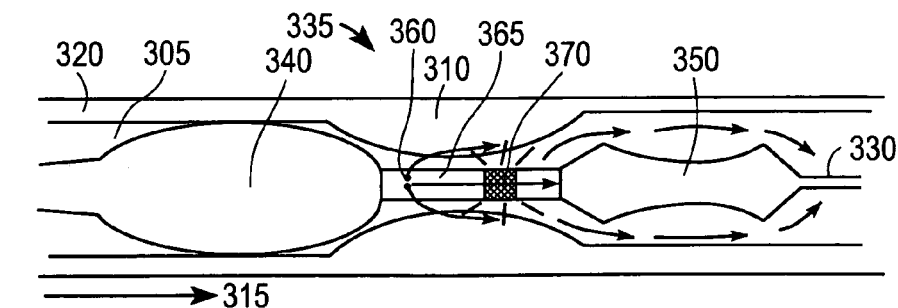

Next, as illustrated in FIG. 3B, first inflatable member 340 expands to block blood flow upstream from plaque 310. Next, as illustrated in FIG. 3C, infusion ports 360 release a light activated drug (indicated by arrows 365) that spreads towards plaque 310 and downstream in the direction of second inflatable member 350. Next, as illustrated in FIG. 3D, light diffuser 370 releases light to activate light drug 365 released from infusion ports 360. Lastly, as illustrated in FIG. 3E, second inflatable member 350 expands to limit the downstream flow of light activated drug 365.

As discussed above, second inflatable member 350, when fully expanded, does not form a seal around arterial lumen 305 when it is desired to allow a downstream flow past the second inflatable member 350. The shape of second inflatable member 350 is such that fluid passes around second inflatable member 350. In one embodiment, second inflatable member 350 may have a series of perfusion paths around the outer surface. In another embodiment, second inflatable member 350 may be a helical balloon in which a perfusion path spirals around the outer surface (e.g., FIG. 6). It will be appreciated that the second inflatable member 350, is an alternative embodiment, may completely cut off any downstream flow when it is not desirable to have such downstream flow.

In an alternative method, first inflatable member 340 expands to block blood flow upstream from the plaque 310. Next, second inflatable member 350 expands to limit down stream flow. Third, infusion ports 360 release a light activated drug that spreads towards plaque 310, and downstream in the direction of second inflatable member 350. Next light diffuser 370 releases light to activate light drug 365 released from infusion ports 360.

Second inflatable member 350 allows light activated drug 365 to remain near plaque 310 of the target treatment area to increase the resonance time that drug 365 can diffuse into the vessel wall 320 of plaque 310. In doing so, the efficiency of the drug may be increased. Additionally, as discussed above, light activated drug 365 may be part of an oxygenated cardioplegia solution. As such, because second inflatable member 350 does not completely block downstream flow, the solution of oxygenated cardioplegia released from infusion ports 360 may supply oxygen to downstream tissue, thereby preventing ischemia. Alternatively, catheter 300 may be used to release a non-light activated drug from infusion ports 360. Second inflatable member 350 would still be effective in increasing the resonance time of any type of drug released, and, if part of an oxygenated cardioplegia solution, would provide oxygen to tissue downstream from catheter 300.

Figure 4:
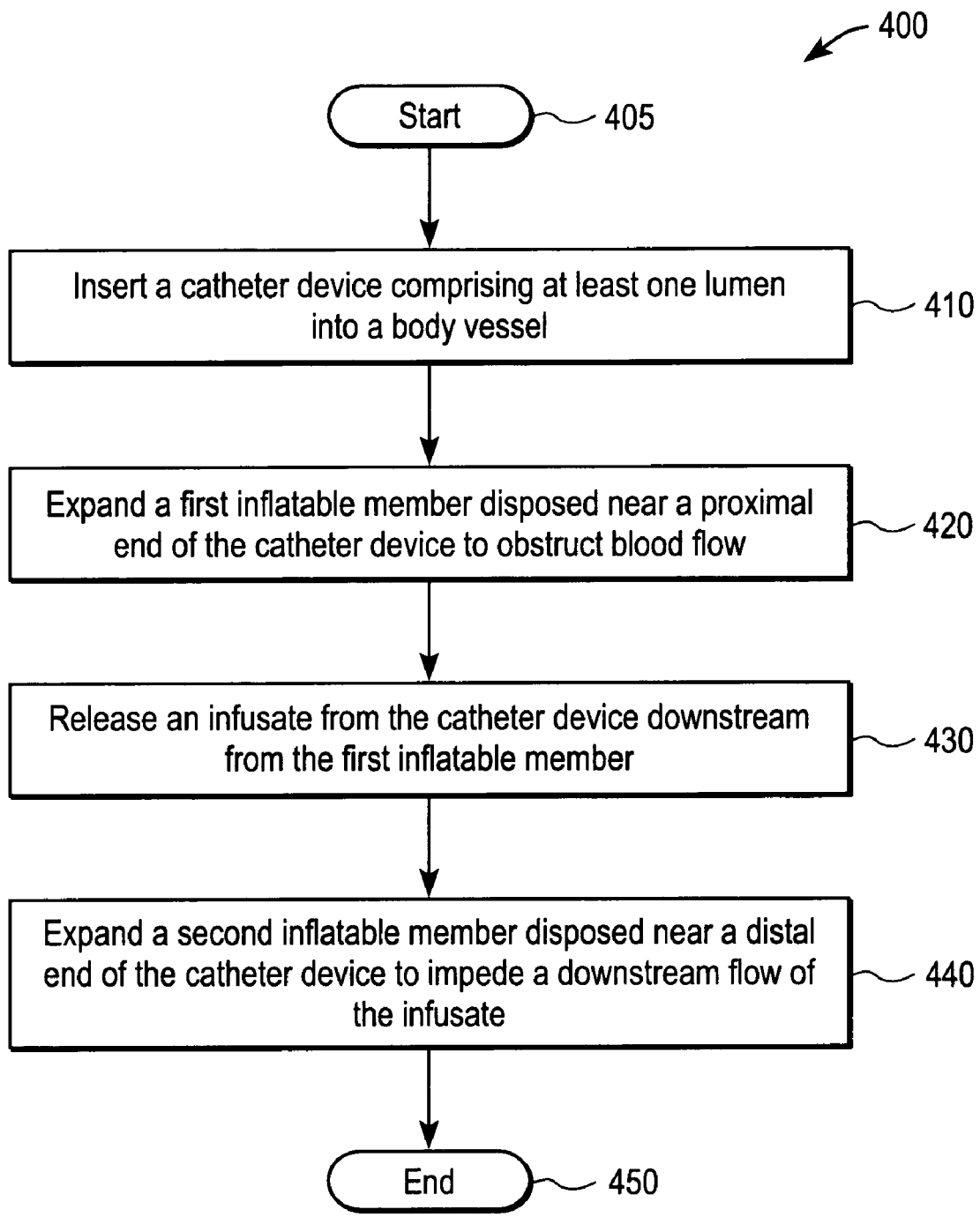
FIG. 4 illustrates, in flowchart form, one method of using a drug delivery catheter.
Figure 5:
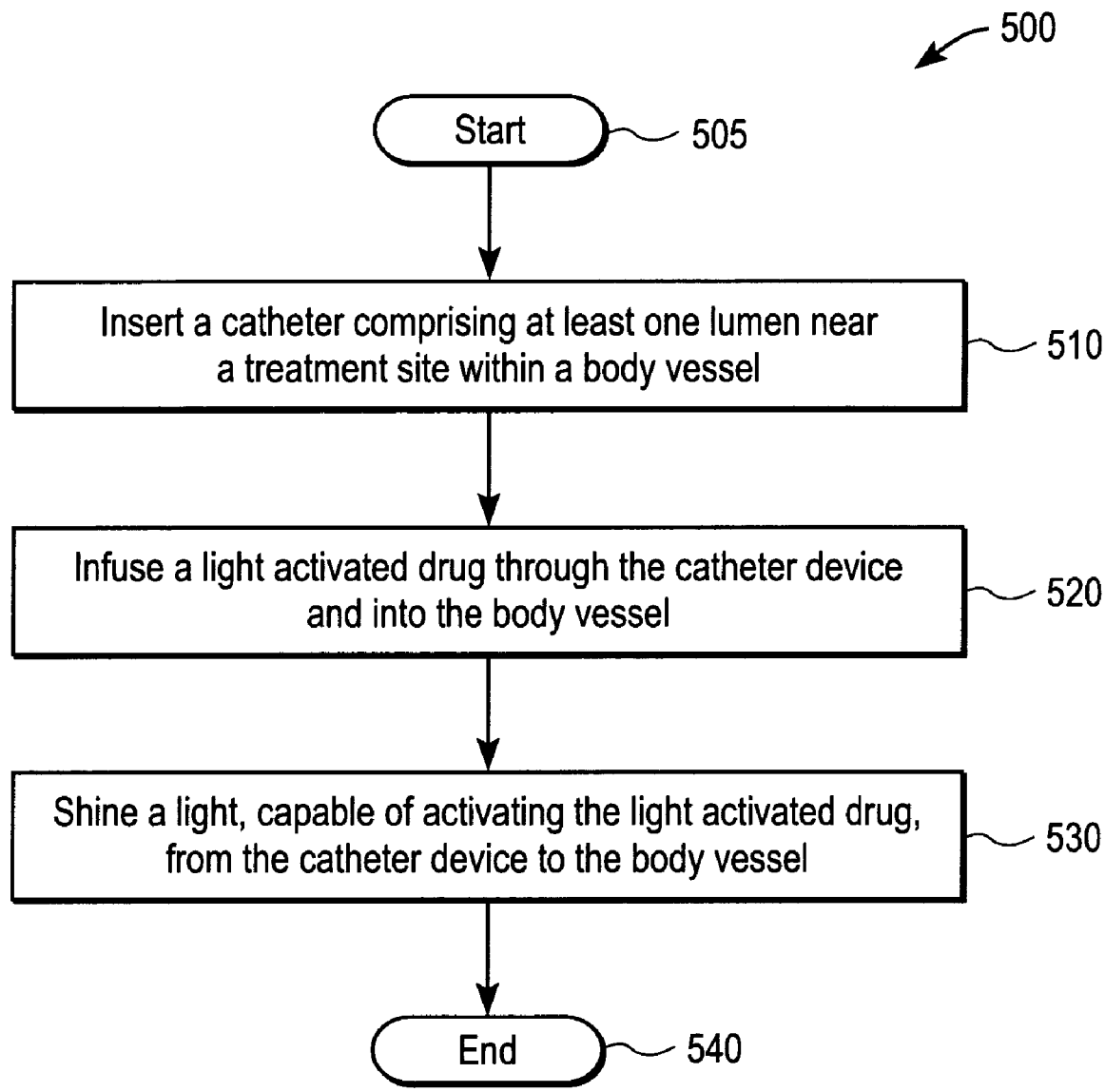
FIG. 5 illustrates, in flowchart form, another method of using a drug delivery catheter.

FIGS. 4 and 5 illustrate, in flowchart form, embodiments of methods of using a drug delivery catheter. The method 400 described in FIG. 4 starts at block 405, followed by block 410 in which a catheter device having at least one lumen is inserted into a body vessel. Next, at block 420, a first inflatable member, disposed near a proximal end of the catheter device, is expanded to obstruct blood flow. At block 430, an infusate is released from the catheter device downstream from the first inflatable member. At block 440, a second expandable member, disposed near a distal end of the catheter device, is expanded to impede downstream flow of the infusate. The method ends at block 450.

FIG. 5 illustrates another embodiment of a method of using a drug delivery device. The method 500 described in FIG. 5 starts at block 505, followed by block 510 in which a catheter device having at least one lumen is inserted into a body vessel. Next, at block 520, a light activated drug is infused through the catheter device and into the body vessel. At block 530, the drug is activated by shining (radiating) a light of a particular intensity from the catheter device to the surrounding area where the drug was released. The method ends at block 540.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A catheter device comprising:
   a first lumen coupled to a first balloon;
   a second lumen coupled to said first lumen, said second lumen having a first distal opening to dispense an oxygenated infusate between said first balloon and a second balloon; and
   a third lumen coupled to said second lumen and coupled to a second balloon, wherein said second balloon reduces the flow of said oxygenated infusate but not completely block the flow of said oxygenated infusate, and wherein said oxygenated infusate provides oxygen to tissue at a distal end of said catheter device, and
   wherein said first balloon is configured to obstruct a fluid flow; and
   wherein said second balloon has a variable diameter that forms perfusion paths along said second balloon outer surface.

2. The catheter device of claim 1, further comprising a fourth lumen coupled to said third lumen, said fourth lumen having an internal dimension designed to receive a guidewire.

3. The catheter device of claim 1, wherein said oxygenated infusate comprises a cardioplegia.

4. The catheter device of claim 1, wherein said first balloon and said second balloon have different shapes from one another.

5. The catheter device of claim 1 wherein said second balloon is a helical balloon.

6. A catheter device comprising:
   a first inflatable member and a second inflatable member;
   an infusion port disposed between said first inflatable member and said second inflatable member, wherein said catheter device, when placed in a body vessel, said first inflatable member inhibits blood flow and said second inflatable member reduces flow of an infusate released from said infusion port but not completely block the flow of said infusate; and
   a light diffuser disposed distal to said infusion port, said light diffuser having a substantially spherical shape and configured to convey light to activate said infusate, and
   wherein said first balloon is configured to obstruct a fluid flow,
   wherein said second balloon has a variable diameter that forms perfusion paths along said second balloon outer surface.

7. The catheter device of claim 6, wherein said second balloon restricts the flow of said infusate and wherein said infusate conveys oxygen to perfuse tissue at a distal end of said catheter device.

8. The catheter device of claim 6, wherein said infusate comprises a cardioplegia.

9. The catheter device of claim 6, wherein said first and second inflatable members comprise balloons.

10. The catheter device of claim 6, wherein said infusate comprises a cardioplegia.

11. The catheter device of claim 6, further comprising a light source disposed between said infusion port and said second inflatable member.

12. The catheter device of claim 11 wherein said infusate comprises a light activated drug.

13. The catheter device of claim 6, wherein said second balloon has a variable diameter that forms perfusion paths along said second balloon outer surface.

14. The catheter device of claim 13 further comprising a light source disposed between said infusion port and said second inflatable member.

* * * * *